United States Patent
Fukami et al.

(10) Patent No.: US 10,132,785 B2
(45) Date of Patent: Nov. 20, 2018

(54) GAS ANALYSIS APPARATUS

(71) Applicant: HORIBA, Ltd., Kyoto (JP)

(72) Inventors: Shun Fukami, Kyoto (JP); Haruhisa Mohara, Kyoto (JP); Shintaro Aoki, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 15/592,992

(22) Filed: May 11, 2017

(65) Prior Publication Data

US 2017/0336375 A1    Nov. 23, 2017

(30) Foreign Application Priority Data

May 17, 2016   (JP) .................................. 2016-099127

(51) Int. Cl.

| | |
|---|---|
| *F16K 15/00* | (2006.01) |
| *G01N 21/03* | (2006.01) |
| *G01N 21/72* | (2006.01) |
| *G01N 27/62* | (2006.01) |
| *G01N 33/00* | (2006.01) |
| *G01N 35/10* | (2006.01) |

(52) U.S. Cl.
CPC ......... *G01N 33/0036* (2013.01); *G01N 21/03* (2013.01); *G01N 21/72* (2013.01); *G01N 27/626* (2013.01); *G01N 33/0024* (2013.01); *G01N 35/1097* (2013.01); *F16K 15/00* (2013.01)

(58) Field of Classification Search
CPC ............................. G01N 27/626; G01N 21/72
See application file for complete search history.

(56) References Cited

U.S. PATENT DOCUMENTS

| | | | |
|---|---|---|---|
| 4,361,810 A | 11/1982 | Schlosser | |
| 5,221,517 A * | 6/1993 | Takeda | G01N 33/0014 422/54 |
| 8,978,444 B2 * | 3/2015 | Chou | G01N 29/022 73/23.42 |

(Continued)

FOREIGN PATENT DOCUMENTS

| | | |
|---|---|---|
| JP | 08035950 A | 2/1996 |
| JP | 09-005299 A | 1/1997 |

OTHER PUBLICATIONS

EESR dated Aug. 2, 2017 issued in European patent application No. 17 171 276.3.

*Primary Examiner* — Shawn Decenzo
(74) *Attorney, Agent, or Firm* — Brooks Kushman P.C.

(57) ABSTRACT

In a gas analysis apparatus including analyzers that need ignition, such as FIDs, in order to make it possible to surely ignite the analyzers while downsizing the entire apparatus, the apparatus includes first and second analyzers to accept a sample gas, a first gas line provided with the first analyzer, a second gas line provided with the second analyzer and joined downstream of the first analyzer in the first gas line. At least one of the first analyzer and the second analyzer is configured to cause pressure fluctuations in the gas line including the analyzer when analyzing the sample gas. A first backflow prevention mechanism is disposed between another of the analyzers and a junction of the gas lines. The first backflow prevention mechanism is configured to prevent a fluid from flowing backward from the one of the analyzers through the junction toward the another of the analyzers.

10 Claims, 7 Drawing Sheets

(56) References Cited

U.S. PATENT DOCUMENTS

| | | | | |
|---|---|---|---|---|
| 9,921,192 B2* | 3/2018 | Chou | ................... | G01N 29/022 |
| 2006/0222563 A1* | 10/2006 | Nakamura | ........... | G01N 27/626 |
| | | | | 422/53 |
| 2008/0014483 A1* | 1/2008 | Kitamura | ................ | C01B 3/323 |
| | | | | 429/416 |
| 2008/0092629 A1* | 4/2008 | Suga | ...................... | A61B 5/097 |
| | | | | 73/28.05 |
| 2010/0172796 A1* | 7/2010 | Norgaard | ............. | G01N 27/626 |
| | | | | 422/54 |
| 2015/0362468 A1* | 12/2015 | Gerhold | ............. | G01N 33/0016 |
| | | | | 73/28.04 |
| 2017/0368539 A1* | 12/2017 | Kubota | .................. | C01B 39/46 |

* cited by examiner

GAS ANALYSIS APPARATUS

CROSS-REFERENCE TO RELATED APPLICATION

This application claims priority to JP Application No. 2016-099127, filed May 17, 2016, the disclosure of which is incorporated in its entirety by reference herein.

BACKGROUND OF THE INVENTION

Field of the Invention

The present invention relates to a gas analysis apparatus to analyze, for example, exhaust gas.

Background Art

As an exhaust gas analysis apparatus, there has conventionally been one which includes a first flame ionization detector (hereinafter referred to as "a first FID") to accept exhaust gas and a second flame ionization detector (hereinafter referred to as "a second FID") to accept the exhaust gas, a first exhaust gas line provided with the first FID, and a second exhaust gas line provided with the second FID, as described in Patent Document 1.

The exhaust gas analysis apparatus includes a filter device disposed only upstream of the second FID in the second exhaust line, and is configured to calculate concentrations of various ingredients and a PM concentration on the basis of a difference between output values of the first FID and the second FID.

Meanwhile, when the exhaust gas analysis apparatus provided with these FIDs is mounted on, for example, a vehicle, there is a desire for downsizing of the entire apparatus. It is therefore desired to commonly use a part of these exhaust gas lines by, for example, causing these exhaust gas lines to be joined downstream of each of the FIDs.

With the above configuration, however, the following problem can occur. Because the exhaust gas lines are joined downstream of each of the FIDs, when one of the FIDs is ignited while the fire of another FID is kept up, air and gas in the exhaust gas line being coupled to one FID may reach another FID, and the fire of another FID may go out under the influence of pressure variations caused by the ignition.

Even with the use of a sequence of concurrently igniting the FIDs, it is difficult to obtain a state in which all of the FIDs are kept burning in the above configuration.

PRIOR ART DOCUMENT

Patent Document

Patent Document 1: Japanese Unexamined Patent Publication No. 9-5299

SUMMARY OF THE INVENTION

Problems to be Solved by the Invention

Accordingly, the present invention has been made to solve the above problem, and has for its main object to make it possible to surely ignite analyzers that need igniting, such as FIDs, in an exhaust gas analysis apparatus, while downsizing the entire apparatus.

Means of Solving the Problems

A gas analysis apparatus according to the present invention includes first and second analyzers to accept a sample gas, a first gas line on which the first analyzer is arranged, and a second gas line on which the second analyzer is arranged and the second gas line is joined with the first gas line downstream of the first analyzer. At least one of the first analyzer and the second analyzer is configured to cause pressure fluctuations in the gas line on which the at least one of the analyzers is arranged when analyzing the sample gas. At least one of a first backflow prevention mechanism and a pressure fluctuation reduction mechanism is disposed between another of the analyzers and a junction of the gas lines. The first backflow prevention mechanism is configured to prevent a fluid from flowing backward from the one of the analyzers through the junction toward the another of the analyzers. The pressure fluctuation reduction mechanism is configured to reduce the pressure fluctuations.

The term "analyzers" is a concept including a filter to collect PM contained in exhaust gas in order to analyze the PM, without being limited to a flame ionization detector to detect ingredients contained in the exhaust gas.

With the above gas analysis apparatus, the entire apparatus can be downsized because the gas lines are joined downstream of the analyzers.

Additionally, because the first backflow prevention mechanism is disposed between another of the analyzers and the junction of the gas lines, the first backflow prevention mechanism is capable of preventing the fluid from flowing backward toward the another of the analyzers due to pressure fluctuations caused, for example, when igniting one of the analyzers. Therefore, for example, when the analyzers are flame ionization detectors, another of the flame ionization detectors is firstly ignited and one of the flame ionization detectors is thereafter ignited. In this way, it is possible to ignite both of the flame ionization detectors.

In order to ensure that both of the analyzers can be ignited irrespective of the order of ignition, a second backflow prevention mechanism is preferably disposed between the one of the analyzers and the junction. The second backflow prevention mechanism is configured to prevent a fluid from flowing backward from the another of the analyzers through the junction toward the one of the analyzers.

As an embodiment with which the effect of the present invention is produced remarkably, there is, for example, such a configuration that at least one of the first analyzer and the second analyzer is a flame ionization detector or a flame photometric detector.

A buffer part is preferably disposed between the first analyzer or the second analyzer and the junction. The buffer part is configured to flatten pressure fluctuations caused when igniting the flame ionization detector or the flame photometric detector which is one of the analyzers, before the pressure fluctuations reach another of the analyzers.

With this configuration, the backflow of the fluid is preventable by both of the backflow prevention mechanism and the buffer part, thereby more surely preventing the fire being kept up from going out, even if the pressure fluctuations due to the ignition of the flame ionization detector as being one of the analyzers is large and the force of the fluid flowing backward to another analyzer is strong, or even if the pressure resistance of the backflow prevention mechanism is low.

In order to dispose the buffer part without enlarging the entire apparatus, the buffer part is preferably formed by making a piping member interposed between one of the analyzers and the junction into a spiral shape.

A suction pump is preferably disposed downstream of the junction. The first gas line and the second gas line is preferably configured to be depressurized by the suction pump.

With this configuration, both of the gas lines can be depressurized by the single suction pump, thereby downsizing the entire apparatus.

Because when, for example, a check valve is used as the backflow prevention mechanism, an operational failure can occur if water drops attach to the check valve, a heating mechanism configured to heat the first analyzer and the second analyzer is preferably further included, and the backflow prevention mechanism is preferably disposed at a position at which no condensation occurs under reduced pressure by the suction pump.

When the backflow prevention mechanism is the check valve, the backflow of the fluid is preventable with a simple and inexpensive configuration.

As a specific embodiment, each of the first analyzer and the second analyzer is a flame ionization detector. A nonmethane cutter is disposed upstream of the second analyzer in the second gas line. The first analyzer is configured to detect total hydrocarbon contained in the sample gas. The second analyzer is configured to detect methane contained in the sample gas.

When the exhaust gas analysis apparatus is configured to be mounted on a vehicle, the effect of the present invention is produced more remarkably.

Effect of the Invention

With the present invention so configured, the exhaust gas analysis apparatus with the FIDs is downsizable as a whole, and each of the FIDs is surely ignited.

DESCRIPTION OF THE EMBODIMENTS

One embodiment of a gas analysis apparatus according to the present invention is described below with reference to the drawings.

Figure 1:
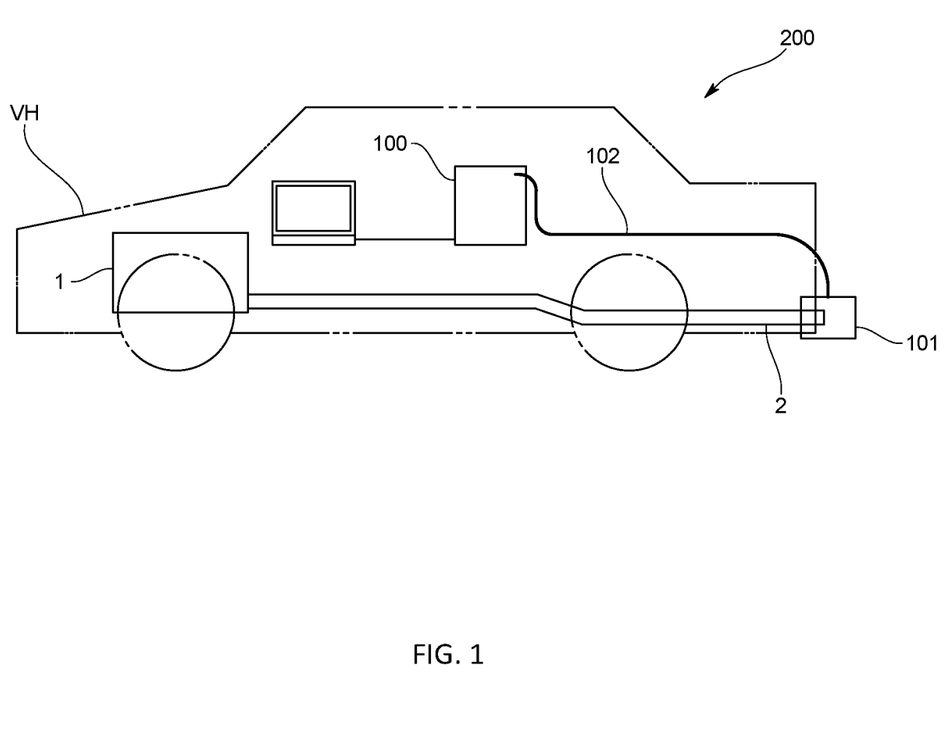
FIG. 1 is a schematic diagram that shows a general configuration of an exhaust gas analysis system of the present embodiment.

As shown in FIG. 1, the gas analysis apparatus 100 of the present embodiment is an on-vehicle type to be mounted on a vehicle VH (hereinafter also referred to as "an exhaust gas analysis apparatus 100"). The gas analysis apparatus 100 constitutes an exhaust gas analysis system 200 together with an exhaust gas collection mechanism 101 and a heated tube unit (hot hose) 102. The gas analysis apparatus 100 is one of various exhaust gas analysis apparatuses to analyze carbon monoxide (CO), carbon dioxide ($CO_2$), nitrogen oxide ($NO_x$), and hydrocarbon (HC), which are contained in exhaust gas.

The exhaust gas analysis system 200 is briefly described below. All or part of exhaust gas is configured to be collected by the exhaust gas collection mechanism 101 attached to an opening-side end of an exhaust pipe 2 being coupled to an internal combustion engine 1 (engine), and the collected exhaust gas is introduced into various exhaust gas analysis apparatuses while heating or maintaining the collected exhaust gas at a predetermined temperature by the heated tube unit 102.

Figure 2:
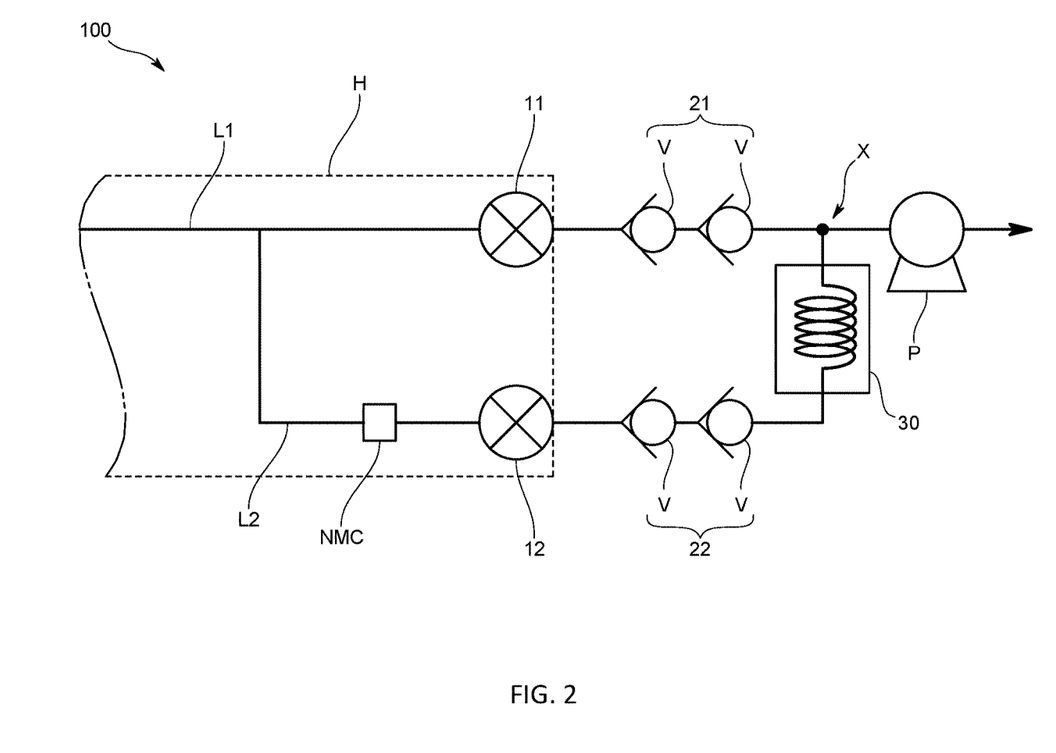
FIG. 2 is a schematic diagram that shows a configuration of an exhaust gas analysis apparatus of the embodiment.

The exhaust gas analysis apparatus 100 of the present embodiment measures a concentration (quantity) of hydrocarbon (HC) that is an organic compound contained in exhaust gas. Specifically, the exhaust gas analysis apparatus 100 includes, as shown in FIG. 2, a first flame ionization detector 11 (hereinafter also referred to as "a first FID 11") as a first analyzer to accept exhaust gas, and a second flame ionization detector 12 (hereinafter also referred to as "a second FID 12") as a second analyzer to accept exhaust gas, a first gas line L1 (hereinafter also referred to as "a first exhaust gas line L1") which is provided with the first FID 11 and coupled to the heated tube unit 102, and a second gas line L2 (hereinafter also referred to as "a second exhaust gas line L2") which is provided with the second FID 12 and branched from upstream of the first FID 11 in the first exhaust gas line L1 and joined downstream of the first FID 11.

The first FID 11 and the second FID 12 are ones which use so-called flame ionization method and are configured to be capable of continuously measuring the concentration of hydrogen carbon (HC) in the exhaust gas on the basis of an ion current generated when the exhaust gas is introduced into a hydrogen flame.

Figure 3:
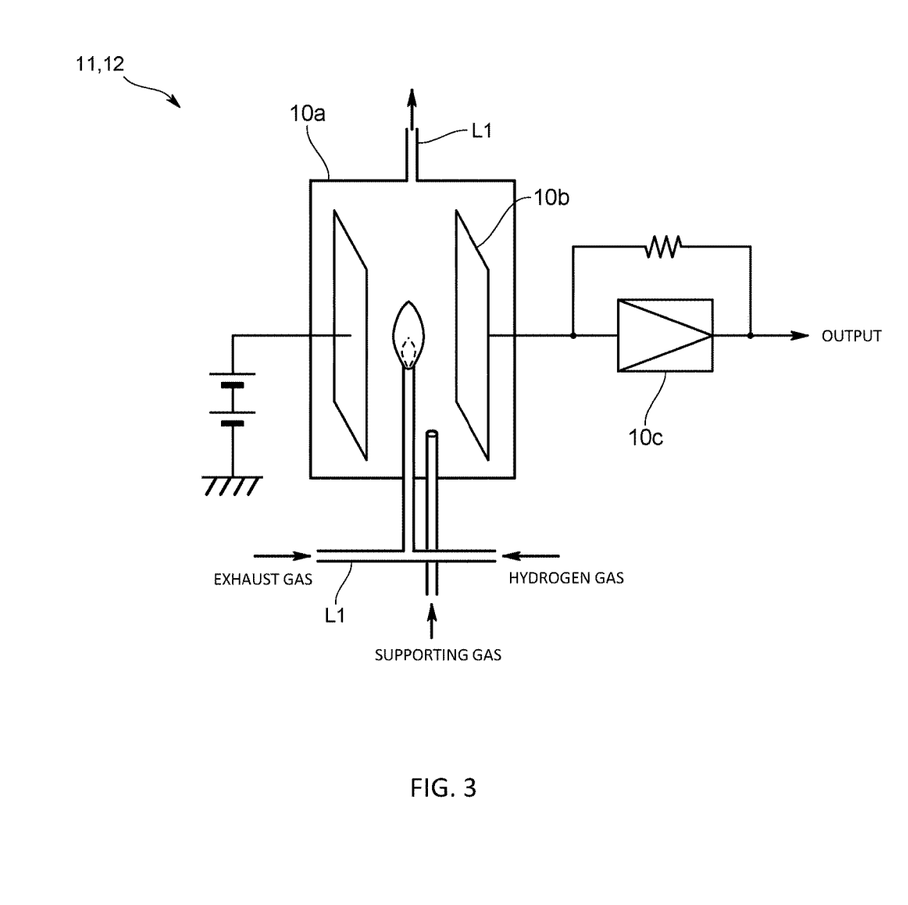
FIG. 3 is a schematic diagram that shows the principle of a flame ionization detector in the embodiment.

Specifically, as shown in FIG. 3, the first FID 11 and the second FID 12 incorporates hydrogen gas and supporting gas (air), which are gases for analysis, into the collected exhaust gas at a certain proportion so as to be burned in a combustion chamber (chimney) 10a with an electric field applied thereto. A collector 10b collects a current generated by ionization of the HC contained in the exhaust gas during the burning. An amplifier 10c amplifies and outputs the current.

Output signals outputted from the first FID 11 and the second FID 12 are transmitted to an information processor (not shown), which calculates a hydrocarbon concentration (quantity) contained in the exhaust gas.

As shown in FIG. 2, the exhaust gas analysis apparatus 100 of the present embodiment includes a nonmethane cutter NMC disposed upstream of the second FID 12 in the second exhaust gas line L2. The exhaust gas analysis apparatus 100 is configured so that the first FID 11 detects total hydrocarbon (THC) in the exhaust gas and the second FID 12 detects methane ($CH_4$) in the exhaust gas. With this configuration, the information processor is capable of calculating a total hydrocarbon concentration and a methane concentration on the basis of the output signals from the first FID 11 and the second FID 12, and also calculating a nonmethane hydrocarbon (NMHC) concentration contained in the exhaust gas on the basis of a difference between the total hydrocarbon concentration and the methane concentration. Here, the detection by the first FID 11 and the detection by the second FID 12 are performed concurrently, and the information processor sequentially calculates the nonmethane hydrocarbon concentration by using detected values respectively obtained from the first FID 11 and the second FID 12.

The exhaust gas analysis apparatus 100 of the present embodiment further includes a heating mechanism H to heat the FIDs 11 and 12 and the exhaust gas lines L1 and L2 in order to prevent condensation of the exhaust gas.

The heating mechanism H heats at least the upstream side of the first FID 11 in the first exhaust gas line L1, and at least the upstream side of the second FID 12 in the second exhaust gas line L2. Here, a setting is made so that the exhaust gas lines L1 and L2 and the FIDs 11 and 12 are heated to 191° C. by using, for example, a heater.

The heating mechanism H is configured to heat the nonmethane cutter NMC disposed in the second exhaust gas line L2 so as to have a higher temperature than the exhaust gas lines L1 and L2. Here, a setting is made so as to heat the nonmethane cutter NMC to 327° C. by using, for example, a heater being different from the above heater.

The exhaust gas analysis apparatus 100 of the present embodiment is configured so that the exhaust gas lines L1 and L2 are depressurized. Specifically, as shown in FIG. 2, the exhaust gas analysis apparatus 100 further includes a suction pump P disposed downstream of a junction X in the first exhaust gas line L1.

The exhaust gas analysis apparatus 100 does not necessarily include the suction pump P, and may alternatively be configured so that exhaust gas is pressurized (forced to enter) from upstream of the first exhaust gas line L1 and the second exhaust gas line L2 so as to be introduced into the FIDs 11 and 12.

In the present embodiment, a first backflow prevention mechanism 21, which prevents a fluid from flowing backward from the junction X toward the first FID 11, is disposed between the first FID 11 and the junction X in the first exhaust gas line L1. A second backflow prevention mechanism 22, which prevents the fluid from flowing backward from the junction X toward the second FID 12, is disposed between the second FID 12 and the junction X in the second exhaust gas line L2.

The first backflow prevention mechanism 21 and the second backflow prevention mechanism 22 are intended to prevent the fluid, such as gas and air, in the exhaust gas lines L1 and L2 being respectively coupled to one of the FIDs 11 and 12 from flowing backward to another of the FIDs 12 and 11 through the junction X due to pressure fluctuations when igniting one of the FIDs 11 and 12. The term "flowing backward" denotes a state in which the gas in the exhaust gas lines L1 and L2 being coupled to one of the FIDs 11 and 12 flows somewhat from the junction X toward another of the FIDs 12 and 11, and the fluid does not necessarily reach another of the FIDs 12 and 11. In other words, it can be said that the backflow prevention mechanisms 21 and 22 prevent the pressure fluctuation when igniting one of the FIDs 11 and 12 from propagating to another of the FIDs 12 and 11.

The first backflow prevention mechanism 21 and the second backflow prevention mechanism 22 are so configured as to block the flow of the fluid from the junction X toward the FIDs 11 and 12 without blocking the flow of the fluid from the FIDs 11 and 12 to the junction X. Here, the backflow prevention mechanisms 21 and 22 have the same configuration and are specifically made up of a plurality of check valves V arranged in series in the exhaust has lines L1 and L2.

These check valves V are so arranged as to block the flow of the fluid from the junction X toward the FIDs 11 and 12 without blocking the flow of the fluid from the FIDs 11 and 12 to the junction X. These check valves V are made of, for example, a resin and have a predetermined pressure resistance (for example, 3-5 kPa).

Because an operational failure can occur if water drops attach to the check valves V at locations of the FIDs 11 and 12 from which water comes out during analysis of the exhaust gas, the check valves V of the present embodiment are disposed at positions in the exhaust gas lines L1 and L2, which ensures transfer of heat generated by the heating mechanism H and ensures a temperature at which no condensation occurs under reduced pressure by the suction pump P.

The check valves V of the present embodiment are made of the resin and are respectively disposed at positions at which the check valves V are not directly heated by the heating mechanism H, so as to fall within a predetermined operating temperature range (for example, 5-80° C.). The operating temperature range of the check valves V is not limited to the above range. For example, check valves usable below 5° C., or check valves usable above 80° C. may be used.

The exhaust gas analysis apparatus 100 of the present embodiment further includes a buffer part 30 which is disposed between the first FID 11 or the second FID 12 and the junction X, and which is a pressure fluctuation reduction mechanism to flatten (reduce) pressure fluctuations caused when igniting one of the FIDs 11 and 12, before the pressure fluctuations reach another of the FIDs 12 and 11.

The buffer part 30 is intended to reduce the force (namely, to reduce a flow rate) of the fluid flowing backward from the junction X to the FIDs 11 and 12. Specific examples of the buffer part 30 are a capillary that becomes resistance against the fluid flowing backward from one of the FIDs to the other, and a space to flatten pressure fluctuations of the fluid flowing backward. Here, as shown in FIG. 2, the buffer part 30 is one obtained by making, into a spiral shape, piping members which are interposed between the junction X and the FID 11 and between the junction X and the FID 12, and which constitute the exhaust gas lines L1 and L2. Of course, the pressure fluctuations can be further flattened by elongating a part having the spiral shape or increasing a piping diameter.

The buffer part 30 needs to be disposed somewhere in a range between the first FID 11, the junction, and the second FID 12. In the present embodiment, in order to prevent water drops from attaching to the check valves V, the buffer part 30 is disposed between the first backflow prevention mechanism 21 and the second backflow prevention mechanism 22, more specifically between the junction X in the second exhaust gas line L2 and the second backflow prevention mechanism 22 so that the check valves V are brought closer to the FIDs 11 and 12.

With the exhaust gas analysis apparatus 100 so configured according to the present embodiment, the exhaust gas lines L1 and L2 are respectively joined downstream of the FIDs 11 and 12 while including the FIDs 11 and 12, thus making it possible to downsize the entire apparatus.

Because the backflow prevention mechanisms 21 and 22 are respectively disposed between the first FID 11 and the junction X, and between the second FID 12 and the junction X, it is possible to avoid that due to the pressure fluctuations when igniting one of the FIDs 11 and 12, the fluid flows backward toward the other. Both flame ionization detectors can be ignited by preventing the fire being kept up from going out.

Additionally, because the buffer part 30 is disposed between the second backflow prevention mechanism 22 and the junction X, the backflow of the fluid is preventable by both of the backflow prevention mechanisms 21 and 22 and the buffer part 30, thereby more surely preventing the fire being kept up from going out, even if the pressure fluctuations due to the ignition of one of the FIDs 11 and 12 is large and the force of the fluid flowing backward to the other is strong, or even if the pressure resistance of the backflow prevention mechanisms 21 and 22 is low.

The present invention is not limited to the above embodiment.

Figure 4:
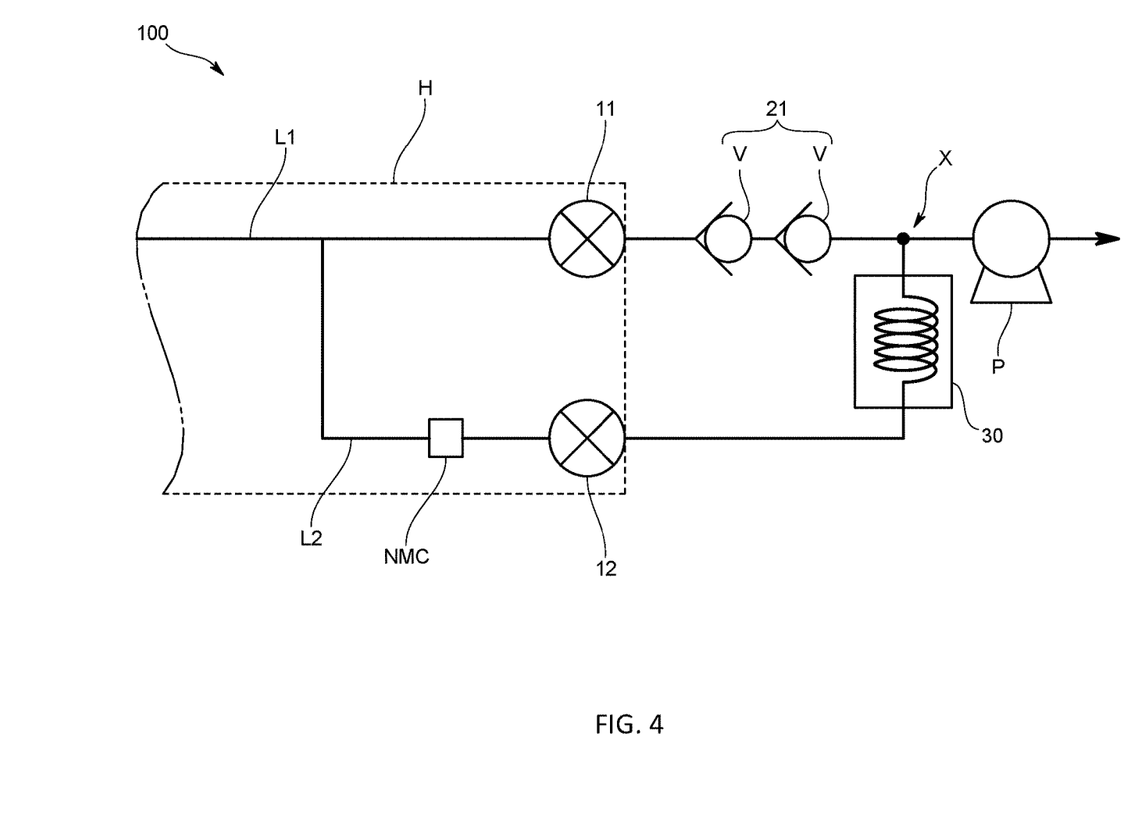
FIG. 4 is a schematic diagram that shows a configuration of an exhaust gas analysis apparatus in another embodiment.

For example, even though the backflow prevention mechanisms are respectively disposed at a location between the first FID and the junction and a location between the second FID and the junction in the above embodiment, the backflow prevention mechanism 21 may be disposed either one of the locations as shown in FIG. 4.

For example, when the backflow prevention mechanism 21 is disposed only at the location between the first FID 11 and the junction X as shown in FIG. 4, the first FID 11 is firstly ignited and the second FID 12 is thereafter ignited. In this way, it is possible to prevent the backflow of the fluid toward the first FID 11 due to the pressure fluctuations when igniting the second FID 12, thereby making it possible to ignite both the FIDs 11 and 12.

Although each of the backflow prevention mechanisms of the above embodiment is made up of the check valves, the backflow prevention mechanisms may be respectively made up of one check valve. The number of the check valves may differ from one backflow prevention mechanism to another.

Alternatively, the backflow prevention mechanisms may be configured to prevent the fluid from flowing backward from the junction to each of the FIDs by having such a structure that an opening/closing valve, such as a solenoid valve, in the first exhaust gas line or the second exhaust gas line. The opening/closing valve is configured to be closed when igniting the first FID or the second FID. In this alternative, by adjusting a valve opening of the opening/closing valve, such as the solenoid valve, the flow rate of the first exhaust gas line and the second exhaust gas line may be controlled so as to reduce, for example, the flow rate of the second exhaust gas line when igniting the first FID.

Still alternatively, the capillary that is a resistance pipe may be employed as the backflow prevention mechanisms.

Moreover, when the backflow prevention mechanisms produce high backflow prevention effect, namely, when the check valves have a high pressure resistance or there are a large number of the check valves, the exhaust gas analysis apparatus does not necessarily include the buffer part.

When the backflow prevention mechanisms produce low backflow prevention effect, the exhaust gas analysis apparatus may have such a structure that a plurality of the buffer parts are disposed between the first FID or the second FID and the junction.

Figure 5:
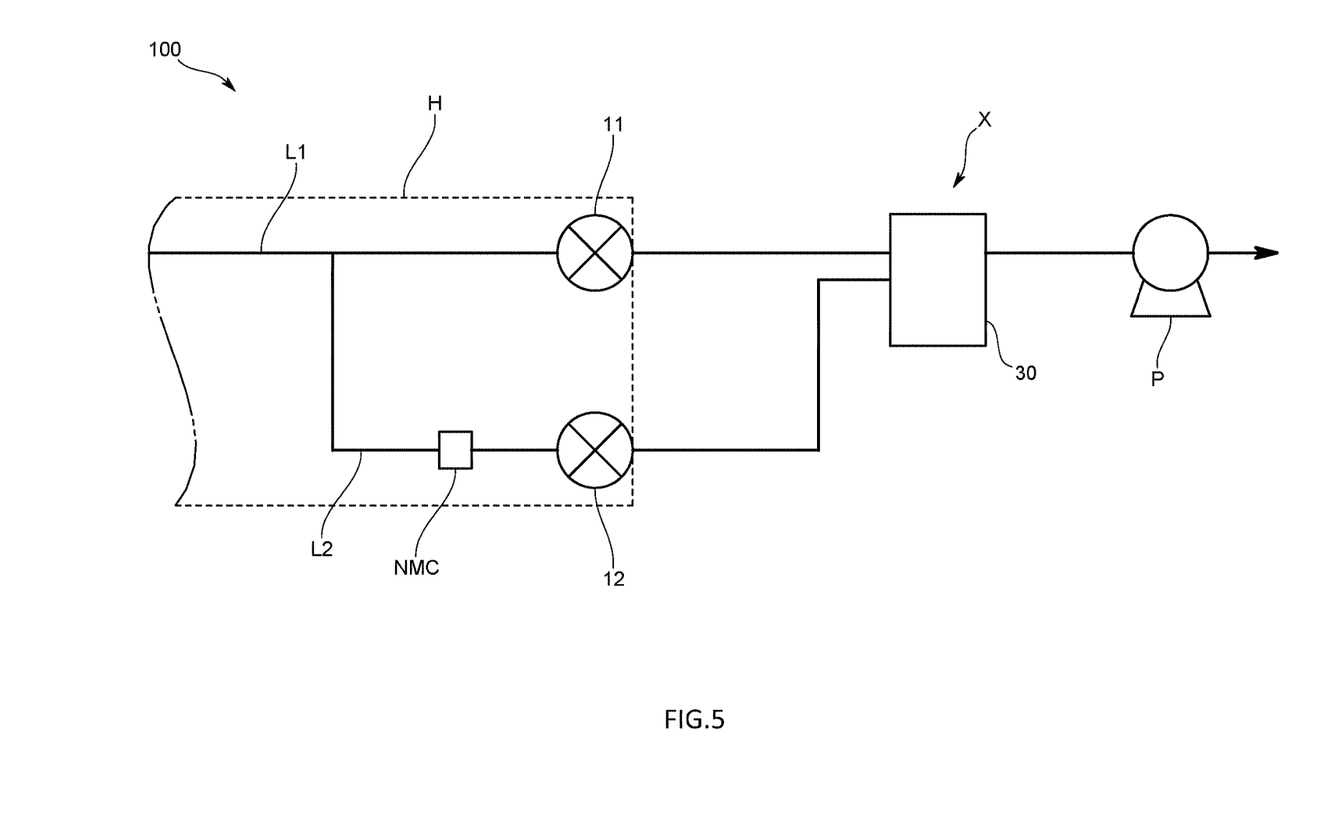
FIG. 5 is a schematic diagram that shows a configuration of an exhaust gas analysis apparatus in still another embodiment.

When the buffer part 30 as the pressure fluctuation reduction mechanism produces high pressure fluctuation reduction effect, the exhaust gas analysis apparatus 100 does not necessarily include the backflow prevention mechanism as shown in FIG. 5.

In this alternative, the buffer part 30 needs to be disposed between the junction X of the first exhaust gas line L1 and the second exhaust gas line L2, and either one of the FIDs 11 and 12. Here, the buffer part 30 is disposed at the junction X as shown in FIG. 5.

Figure 6:
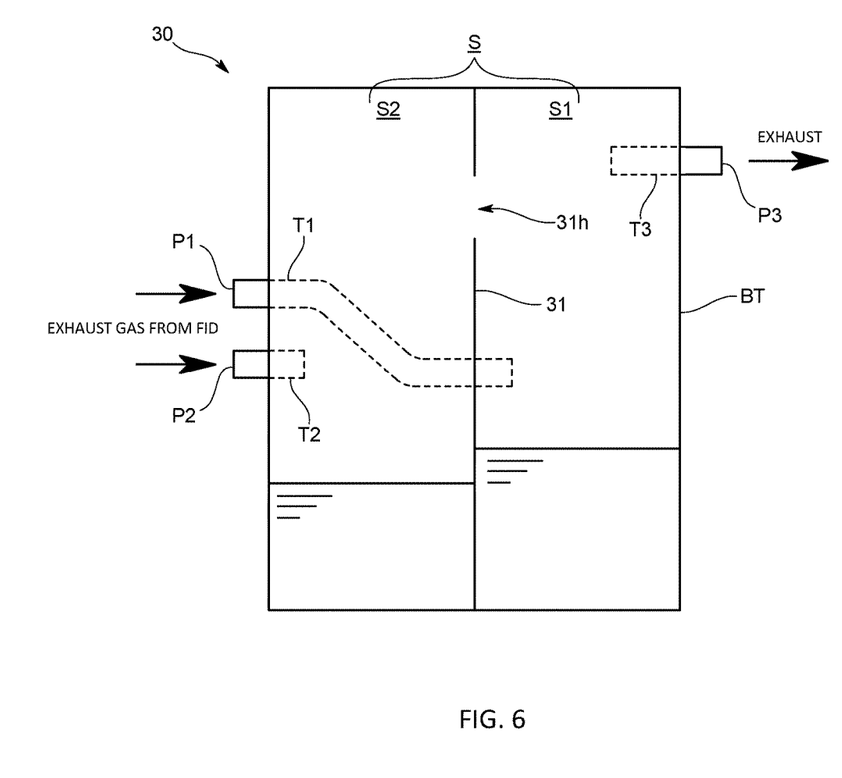
FIG. 6 is a schematic diagram that shows a configuration of a pressure fluctuation reduction mechanism in yet another embodiment.

Specifically, as shown in FIG. 6, the buffer part 30 includes a buffer tank BT having a buffer space S into which exhaust gas discharged from the first FID 11 and exhaust gas discharged from the second FID 12 flow. The buffer tank BT includes a first inflow port P1 to be coupled with the first exhaust gas line L1, a second inflow port P2 to be coupled with the second exhaust gas line L2, and a discharge port P3 through which the exhaust gas flowing into the buffer space S is discharged to the outside. The first inflow port P1 and the second inflow port P2 are respectively upstream-side openings of a first inflow tube T1 and a second inflow tube T2, each penetrating through a sidewall (front surface) of the buffer tank BT. The discharge port P3 is a downstream-side opening of a discharge tube T3 penetrating through a sidewall (back surface) of the buffer tank BT.

Taking into consideration the fact that water discharged from the FIDs 11 and 12 flows into and stay in the buffer space S, the first inflow port P1 and the second inflow port P2 are respectively disposed at positions somewhat higher than a bottom surface of the buffer tank BT in order to prevent the water flowing in the buffer space S from flowing backward to the first inflow port P1 and the second inflow port P2. The buffer tank BT is heated by heat from the FIDs 11 and 12 and the nonmethane cutter NMC, and the buffer space S is under reduced pressure. Therefore, the water remaining in the buffer tank BT is vaporized in the buffer tank BT and then discharged from the discharge port P3.

The buffer part 30 includes a partition member 31 to divide the buffer space S into a first space S1 into which the exhaust gas discharged from the first FID 11 flows, and a second space S2 into which the exhaust gas discharged from the second FID 12 flows.

The partition member 31 divides the buffer space S into an upstream-side space and a downstream-side space. Here, the downstream-side space is taken as a first space S1 and the upstream-side space as a second space S2. The first inflow tube T1 is penetrated through the partition member 31 so that the downstream-side opening of the first inflow tube T1 is disposed in the first space S1.

The partition member 31 has, for example, at an upper part thereof, a communication hole 31$h$ to establish communication between the first space S1 and the second space S2. With this configuration, the exhaust gas flowing into the second space S2 flows through the communication hole 31$h$ into the first space S1 and thereafter exhausted from the discharge port P3.

With the exhaust gas analysis apparatus 100 so configured, the buffer part 30 as the pressure fluctuation reduction mechanism is capable of reducing the pressure fluctuations for example due to the ignition of one of the FIDs 11 and 12, before the pressure fluctuations reach the other. It is therefore avoidable that due to the pressure fluctuations by the ignition of one of the FIDs, the fire being kept up in the other goes out, thus making it possible to ignite both the FIDs 11 and 12.

Figure 7:
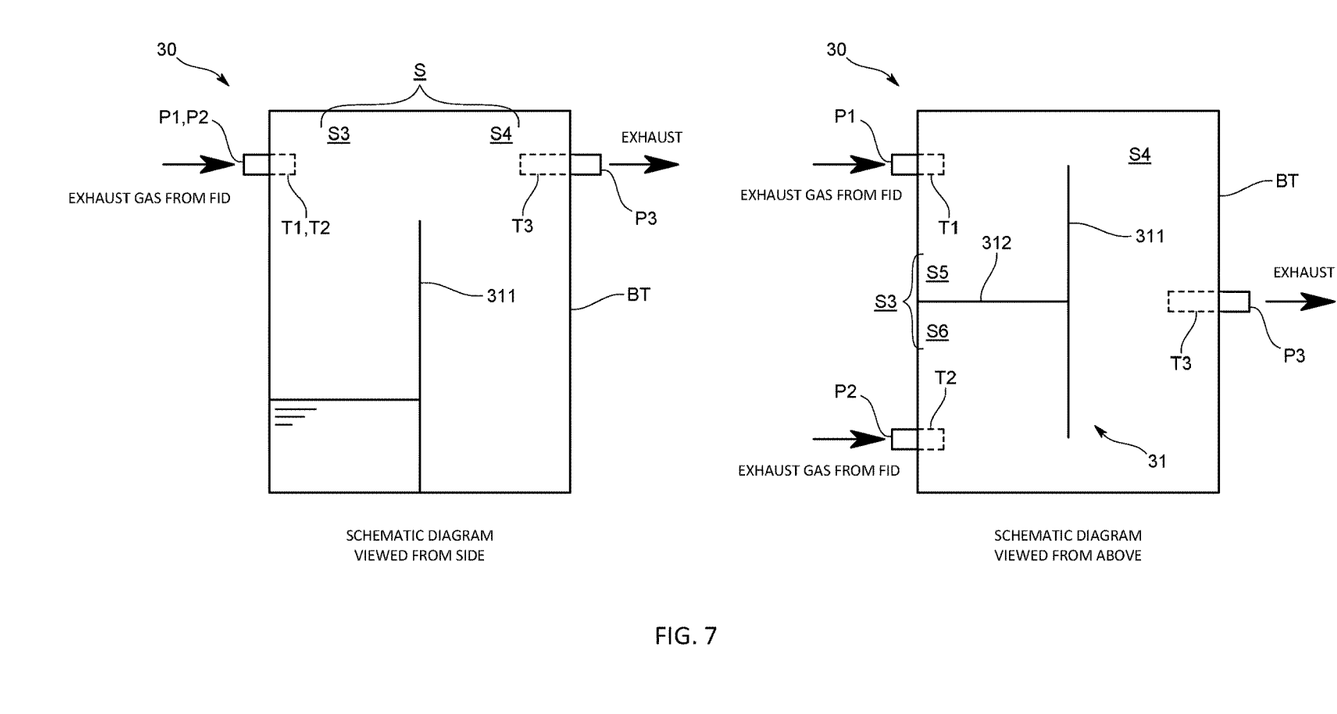
FIG. 7 is a schematic diagram that shows a pressure fluctuation reduction mechanism in further embodiment.

The partition member 31 may be modified suitably as long as it is configured to prevent the exhaust gas from the exhaust gas lines L1 and L2 from directly joining together. For example, the partition member 31 shown in FIG. 7 includes a first partition element 311 and a second partition element 312. The first partition element 311 divides the buffer space S into an upstream-side space S3 and a downstream-side space S4. The second partition element 312 extends in a flow direction of exhaust gas, and divides the upstream-side space S3 into an upstream-side first space S5 into which the exhaust gas from the first exhaust gas line L1 flows, and an upstream-side second space S6 into which the exhaust gas from the second exhaust gas line L2 flows.

As other embodiment, the number of the FIDs included in the exhaust gas analysis apparatus is not limited to two, and the number thereof may be three or more. In this configuration, the exhaust gas lines respectively coupled to the FIDs need to be joined downstream of the FIDs, and the backflow prevention mechanisms need to be disposed between a junction thereof and each of the FIDs.

Ingredients in the exhaust gas to be analyzed in these FIDs are not limited to total hydrocarbon and methane, and may be changed variously.

Although both of the first analyzer and the second analyzer are the FIDs in the present embodiment, for example, one of the analyzers may be one different from the FID, such as a filter to collect PM in exhaust gas in order to analyze the PM.

Thus, when one of the analyzers is the filter, the following problem can occur. That is, under the influence of pressure fluctuations when igniting the other analyzer, namely, the FID, the collected PM may fall off from the filter, leading to measurement error.

Accordingly, even in this configuration, the above problem is soluble by including the first backflow prevention mechanism configured to prevent the fluid from flowing backward from the other analyzer (FID) to one of the analyzers (namely, the filter).

The analyzer different from the FID is not limited to the filter, and may be an analyzer, such as an FTIR.

The first analyzer and the second analyzer are not limited to the FIDs, and may be, for example, a flame photometric detector (FPD), as long as it causes pressure fluctuations due to ignition and burning in the gas line provided with the analyzers when carrying out analysis, specifically before the analysis or during the analysis.

Although the above embodiment has described the on-vehicle type exhaust gas analysis apparatus to analyze the exhaust gas, the exhaust gas analysis apparatus is not limited to the on-vehicle type, and may be, for example, one which analyzes a sample gas in a cylinder.

Besides those mentioned above, it will be understood that the present invention is not limited to the above-described embodiment, and various modifications may be made without departing from the spirit and scope of the present invention.

DESCRIPTION OF THE REFERENCE NUMERAL

100 exhaust gas analysis apparatus
VH vehicle
1 internal combustion engine
11 first FID
12 second FID
L1 first exhaust gas line
L2 second exhaust gas line
X junction
21 first backflow prevention mechanism
22 second backflow prevention mechanism
V check valve
30 buffer part
P suction pump

What is claimed is:
1. A gas analysis apparatus comprising:
first and second analyzers configured to accept a sample gas;
first and second gas lines, joined at a junction downstream of the first analyzer, on which the first and second analyzers are respectively arranged; and
a valve or buffer tank disposed between one of the first and second analyzers and the junction,
wherein the first analyzer is configured to cause pressure fluctuations in the first gas line when analyzing the sample gas or the second analyzer is configured to cause pressure fluctuations in the second gas line when analyzing the sample gas,
wherein the valve is configured to prevent a fluid from flowing backward from the one of the first and second analyzers through the junction toward the other of the first and second analyzers, and
wherein the buffer tank is configured to reduce the pressure fluctuations, and has a buffer space into which exhaust gas discharged from the first and second analyzer flows, first and second inflow ports coupled with the first and second gas lines, and a discharge port through which the exhaust gas is discharged to the outside.

2. The gas analysis apparatus according to claim 1, wherein a second valve is disposed between the one of the first and second analyzers and the junction, and is configured to prevent a fluid from flowing backward from the other of the first and second analyzers through the junction toward the one of the first and second analyzers.

3. The gas analysis apparatus according to claim 1, wherein the first analyzer or the second analyzer is a flame ionization detector or a flame photometric detector.

4. The gas analysis apparatus according to claim 3, wherein the buffer tank is configured to reduce pressure fluctuations caused when igniting the flame ionization detector or the flame photometric detector before the pressure fluctuations reach the other of the first and second analyzers.

5. The gas analysis apparatus according to claim 4, wherein the buffer tank is formed by making a piping member interposed between the one of the first and second analyzers and the junction into a spiral shape.

6. The gas analysis apparatus according to claim 1,
wherein a suction pump is disposed downstream of the junction, and
wherein the first and second gas lines are configured to be depressurized by the suction pump.

7. The gas analysis apparatus according to claim 6, further comprising a heater configured to heat the first and second analyzer,
wherein the valve is disposed at a position at which no condensation occurs under reduced pressure by the suction pump.

8. The gas analysis apparatus according to claim 1, wherein the valve is a check valve.

9. The gas analysis apparatus according to claim 1,
wherein each of the first and second analyzers is a flame ionization detector,
wherein a nonmethane cutter is disposed upstream of the second analyzer in the second gas line,
wherein the first analyzer is configured to detect total hydrocarbon contained in the sample gas, and
wherein the second analyzer is configured to detect methane contained in the sample gas.

10. The gas analysis apparatus according to claim 1 being configured to be mounted on a vehicle.

* * * * *